United States Patent
Doll et al.

(10) Patent No.: US 9,032,958 B2
(45) Date of Patent: May 19, 2015

(54) SUPPORT FOR TRACHEOSTOMY OR ENDOTRACHEAL TUBES

(71) Applicants: Gregory E. Doll, Bethesda, MD (US); Michael Schuster, West Chester, PA (US)

(72) Inventors: Gregory E. Doll, Bethesda, MD (US); Michael Schuster, West Chester, PA (US)

(*) Notice: Subject to any disclaimer, the term of this patent is extended or adjusted under 35 U.S.C. 154(b) by 392 days.

(21) Appl. No.: 13/659,650

(22) Filed: Oct. 24, 2012

(65) Prior Publication Data

US 2013/0174844 A1    Jul. 11, 2013

Related U.S. Application Data

(60) Provisional application No. 61/554,576, filed on Nov. 2, 2011.

(51) Int. Cl.
| | | |
|---|---|---|
| *A61M 16/04* | (2006.01) | |
| *A61M 16/08* | (2006.01) | |
| *A61M 16/00* | (2006.01) | |

(52) U.S. Cl.
CPC ....... *A61M 16/0497* (2013.01); *A61M 16/0465* (2013.01); *A61M 16/0816* (2013.01); *A61M 16/0057* (2013.01); *A61M 16/0875* (2013.01); *Y10S 128/912* (2013.01)

(58) Field of Classification Search
USPC .......... 128/207.14, 207.17, 207.11, 911, 912, 128/205.25
See application file for complete search history.

(56) References Cited

U.S. PATENT DOCUMENTS

| | | | | |
|---|---|---|---|---|
| 3,927,676 | A | * 12/1975 | Schultz | 128/207.17 |
| 4,313,437 | A | 2/1982 | Martin | |
| 4,331,144 | A | 5/1982 | Wapner | |
| 5,101,822 | A | 4/1992 | Kimmel | |
| 5,282,463 | A | * 2/1994 | Hammersley | 128/207.15 |
| 5,357,952 | A | 10/1994 | Schuster | |
| 5,671,732 | A | * 9/1997 | Bowen | 128/207.17 |
| 6,047,699 | A | 4/2000 | Ryatt | |
| 7,635,000 | B2 | * 12/2009 | Wilson et al. | 128/207.17 |
| 8,074,650 | B2 | * 12/2011 | Steeves et al. | 128/207.17 |

* cited by examiner

*Primary Examiner* — Steven Douglas
(74) *Attorney, Agent, or Firm* — Jeffrey S. Melcher; Manelli Selter PLLC

(57) ABSTRACT

A device for securing a tracheostomy or endotracheal tube to a patient.

3 Claims, 3 Drawing Sheets

SUPPORT FOR TRACHEOSTOMY OR ENDOTRACHEAL TUBES

This application claims priority to U.S. Provisional Patent Application No. 61/554,576, filed 2 Nov. 2011, the complete disclosure of which is incorporated herein by reference.

FIELD OF THE INVENTION

The invention relates to a device for securing a tracheostomy or endotracheal tube to a patient.

BACKGROUND OF THE INVENTION

Tracheostomy or endotracheal tubes are often placed in severely injured or ill patients to assist them in breathing. In many instances, a ventilator is connected to the tube to provide controlled ventilation.

Patients with tracheostomy tubes and ventilator circuitry are many times severely compromised and ill due to associated complications. Existing in these patients are various complications from tube movement, circuitry weight and accidental circuitry disconnections. These complications can create discomfort, skin, stoma and tracheal irritation, skin, stoma and tracheal malacia, leading to potential infections and surgical intervention, brain injury or death. The unintended pressure from the weighty and moving circuitry may result in tubing disconnection, Stoma site damage and posterior wall tracheal damage from improper tube positioning.

Tracheostomy and endotracheal tubes were customarily supported in place by a thin cotton tape extending about the neck or head of a patient. The cotton tape was typically tied to slotted flanges on either side of the tube to secure it in place. This method for securing a tracheostomy or endotracheal tube has many drawbacks. The cotton tape had to be threaded through and knotted to each flange or separate pieces had to be threaded through the flanges and then tied to each other to secure the tube. There was no convenient means for securing and/or adjusting the cotton tape to ensure a proper fit. This could result in a poorly secured or mislocated tracheostomy tube, contributing to the potential for injury of the soft tissues surrounding the stoma of a tracheostomy.

The cotton tape utilized to secure the tube also has a tendency to stretch more at the edges than at the center as it is being installed, and the tying process further distorts the tape. This results in an uneven force distribution across the width of the tape causing patient discomfort and possible skin irritation. This condition is evidenced by the typical curl at the edges of the cotton tape.

Because of the degree of intensive care required in using tracheostomy or endotracheal tubes and their accompanied tubing and circuitry, ease in maintaining the tracheostomy tube through adjustment or replacement of the retention means is also a prime concern. Not only must the retention means be easy to install and adjust, but asepsis concerns make it desirable that the retention means be low cost, soft fabric, skin friendly and therefore disposable.

U.S. Pat. No. 4,313,437 to Martin, issued Feb. 2, 1982, and U.S. Pat. No. 4,331,144 to Wapner, issued May 25, 1982 have attempted to address some of these problems. Both show the use of a padded foam neck band and VELCRO™ fastening means. These provide easier installation, replacement and adjustment as well as more even force distribution and patient comfort. Although the tube retainer disclosed by Martin does provide for some expansion or contraction once installed, it has limited adjustability and several sizes are required for different size patients.

The support provided by Wapner involves a more complex structure. It utilizes two straps, one of which has an elastic webbing portion. This is to allow the attendant applying the band to select a comfortable pressure for securing the band to the patient. Because of its more complex structure, this support band is more costly to manufacture.

U.S. Pat. No. 5,101,822 (Kimmel), issued Apr. 7, 1992, also attempts to address these problems. Kimmel discloses a two-piece collar system which appears complex and requires the alignment of snaps on the two collar pieces and threading tapes from one collar piece through loops in the other for installation. This more complex structure could increase the cost of the device making disposable usage cost prohibitive.

U.S. Pat. No. 5,357,952 (Schuster), issued Oct. 25, 1994 addresses these problems by disclosing a collar with a complex buckle and long securement strap to retain circuitry. However, the buckle system is found to be difficult to engage and the hard, hook material used on the long strap may potentially lead to skin irritation and skin breakdown issues as well as difficulty in application of securement strap.

None of these devices provide a means for positively retaining a ventilator tube connection to the tracheostomy tube in an uncomplicated method without risking skin irritation and infection risks.

SUMMARY OF THE INVENTION

An objective of the invention is to provide an adjustable neckband for securing tracheostomy, endotracheal, or other medical tubes to a patient.

Another objective of the invention is to provide a soft fabric medical tube support having skin friendly soft fabric with means for releasably securing a connector to the tube, to reduce possible skin irritation.

A further objective of the invention is to provide ventilator fastener having a tapered distal end tab that will slide without interference into the neckflange slots of small and pediatric sized tracheostomy and endotracheal tubes, and having a skin friendly soft fabric to reduce possible skin irritation.

Another objective of the invention is to provide a disposable means for securing a tube to a patient.

A further objective of the present invention is to overcome the pressure from the weighty and moving circuitry that may result in stoma site damage and back wall tracheal damage from improper tube positioning.

The present invention replaces the conventional hard plastic hook (Velcro) material of the ventilator fastener with a softer textile material having a hook surface on the distal end to secure the strap to the neck band. This adaptation reduces the chance of skin irritation and skin breakdown if this fastener contacts the patient's skin.

The present invention also replace the conventional adhesive loop patch used to secure the previous hook strap with an adhesive hook surface that will mate (Velcro) with the new embodiment comprising of the soft fabric anti-disconnect strap and support.

The present invention also removes the conventional elastic piece in the neckband previously installed to accommodate edema or the cough reflex. Clinical observation and practical experience has demonstrated that the "play or give" that the elastic affords in the neckband actually allows for too much expansion possibly contributing to accidental disconnections of the circuitry from a 15 mm connector of the Tracheostomy tube.

The present invention also provides tapering of pediatric trach tube neckband hook tabs. The hook tabs or Velcro fasteners on either end of the pediatric trach tube holder neckbands are in many cases too wide to slide comfortably through the small neckflange slots of a pediatric tracheostomy tubes. As clinicians attempt to manipulate and forcefully pull the oversized tabs through the undersized pediatric neckflange slots skin irritation and potential skin breakdown results. This patent modification will effectively reduce the neckband tab sizing and taper the ends to easily and smoothly slide through the trach tube neckflange slot reducing potential skin trauma.

The soft fabric textile strap made of soft fabric will wrap in a secure manner to lift the tubing and reposition the distal end of the tracheostomy tube and reduce pressure on the stoma site and back wall of the trachea. The unintended pressure from the weighty and moving circuitry may result in stoma site damage and back wall tracheal damage from improper tube.

These objectives and other objectives are obtained by a device for securing a medical tube comprising a tracheostomy or endotracheal tube and a slotted flange having a first and a second slot, said device constructed to retain the medical tube to a ventilator tube connector, the device comprising:

a neckband having a first and a second end, the neckband comprising an interior foam material, an inner textile surface suitable for placement against human skin, and an outer textile fastening material;

a neckband fastening strip having a first end and a second end, the first end of the neckband fastening strip being connected to the first end of the neckband, the neckband and neckband fastening strip having a length sufficient to encircle a human neck, a majority of a length of the neckband fastening strip comprising a non-hook, textile material, the second end of the neckband fastening strip having a hook face surface constructed to releasably fasten to the outer textile fastening material, the second end of the neckband fastening strip being tapered and the neckband fastening strip being sized for insertion into the first and second slots when the flange is pediatric sized; and a ventilator fastener comprising a textile strip having a first end and second end, the textile strip comprising an inner surface that is suitable for placement against skin, the first end of the ventilator fastener being connected to the first end of the neckband, the second end of the ventilator fastener constructed to releasably fasten to the outer textile fastening material, and the ventilator fastener having a length sufficient to encircle a connector and have the second of the ventilator fastener fasten to the outer textile fastening material.

These objectives and other objectives are further obtained by a method of securing a medical tube comprising a tracheostomy or endotracheal tube and a slotted flange having a first and a second slot using a device, the method comprising:

providing the device comprising:

a neckband having a first and a second end, the neckband comprising an interior foam material, an inner textile surface suitable for placement against human skin, and an outer textile fastening material;

a neckband fastening strip having a first end and a second end, the first end of the neckband fastening strip being connected to the first end of the neckband, the neckband and neckband fastening strip having a length sufficient to encircle a human neck, the neckband fastening strip comprising a non-hook, textile material, the second end of the neckband fastening strip having a hook face surface constructed to releasably fasten to the outer textile fastening material, the second end of the neckband fastening strip being tapered and the neckband fastening strip being sized for insertion into the first and second slots when the flange is pediatric sized; and a ventilator fastener comprising a textile strip having a first end and second end, the textile strip comprising an inner surface that is suitable for placement against skin, the first end of the ventilator fastener being connected to the first end of the neckband, the second end of the ventilator fastener constructed to releasably fasten to the outer textile fastening material, and the ventilator fastener having a length sufficient to encircle a connector and have the second of the ventilator fastener fasten to the outer textile fastening material; cutting the neckband to fit a patient's neck if the neckband is too long for the patient;

placing the neckband fastening strip through slots in the flange and fastening the second end of the fastening strip to the second end of the neckband so that the portion of the fastening strip in contact with the patient's skin is free of a hook surface; and wrapping the ventilator fastener around the connector and fastening the second end of the ventilator fastener to the second end of the neckband so that the portion of the ventilator fastener in contact with the patient's skin is free of a hook surface.

DETAILED DESCRIPTION OF THE INVENTION

The invention will now be explained with reference to the attached non-limiting Figs.

Figure 1:
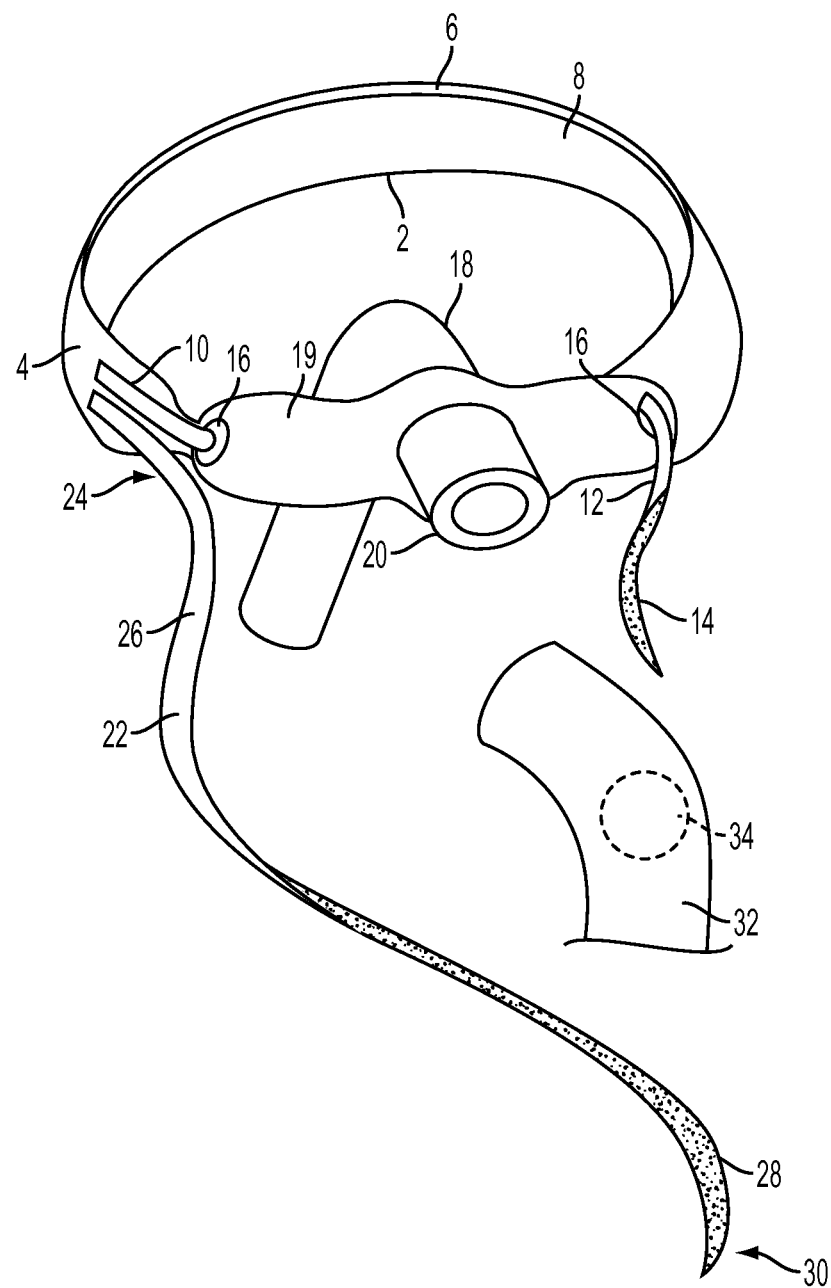
FIG. 1 is a perspective view of an embodiment of the invention with the strap in an open position.
Figure 2:
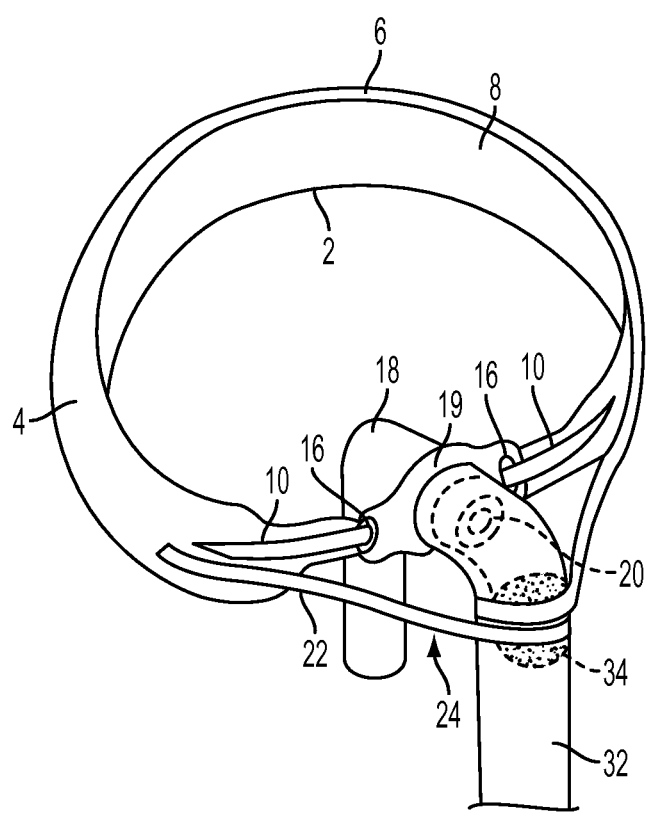
FIG. 2 is a perspective view of an embodiment of the invention with the strap in a fastening position.
Figure 3:
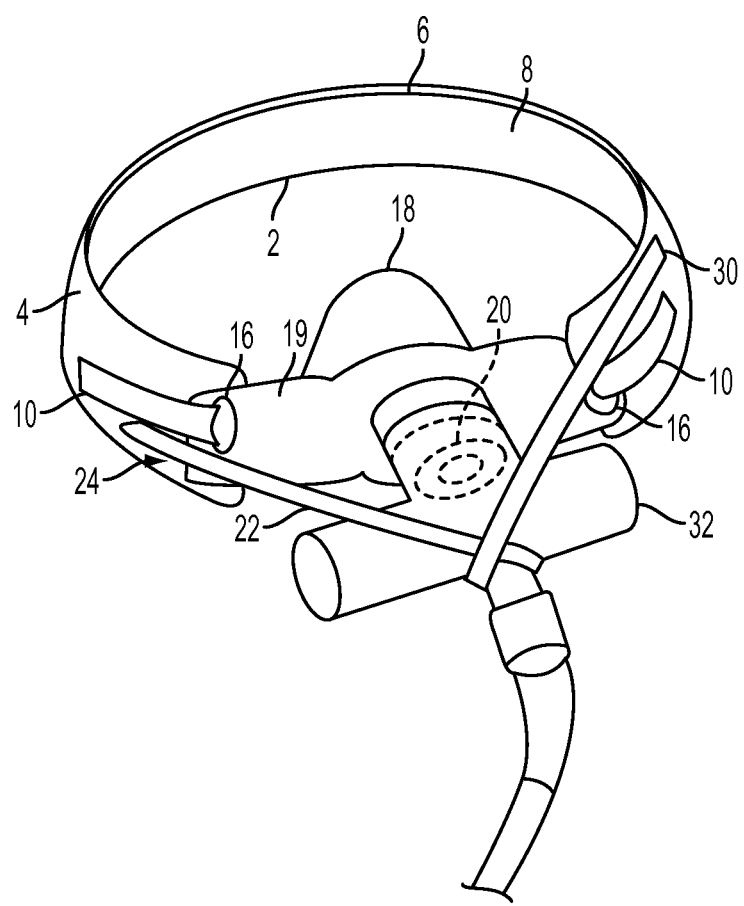
FIG. 3 is a perspective view of an embodiment of the invention with the strap in a fastening position.

Referring to FIG. 1-3, there is shown a tube retention device according to the present invention. The tube retention device comprises a neckband 8 comprising a material suitable for contact to human skin. A suitable example of the neckband 8 is an inner textile layer 2, an outer textile layer 4 and a foam interior layer 6. The interior layer 2 is a soft fiber lining which will lay against the patient's skin to prevent irritation. The exterior layer 4, for example, can be formed from a textile fastener material such as a loop type textile fastening material sold under the trademark VELCRO™. A non-limiting exemplary size of the neckband 8 is about 1 inch wide and about 18 inches long.

Affixed to one end of the neckband 8 is a neckband fastening strip 10. A first end of the fastening strip 10 is permanently attached to a first end of the neckband 8. As will be recognized by those skilled in the art, the neckband is placed around the patient's neck, and the length of the neckband 8 is adjusted by trimming the second end opposite from the first end. The second free end 14 of the fastening strip 10 is passed through slots 16 in the neck flange 19 of a tracheostomy or endotracheal tube 18 to a position above the loop-type textile fastening material of the outer layer 4 where the second end 14 is releasably secured top the outer layer 4 so that the neckband 8 snuggly fits around the patient's neck. The second end 14 preferably comprises a hook face (Velcro) that can releasably attach to the textile surface 4. In this manner, the tube 18 is held firmly in place. Since the length of the neckband 8 can be adjusted by trimming the end to which the removable fastening strip 10 will be secured prior to its installation, the medical tube retention device can be produced in a single size and be trimmed during installation to provide a custom fit for each patient. The end 14 of the strip 10 is preferably tapered and sized to permit easy insertion into the slots 16 of a pediatric sized connector 32. An example of a size for the end 14 of the strip 10 is about ³⁄₁₆ of an inch or less in width.

As is known in the art, a ventilator connector 32 is frequently attached to the connector 20 of the tracheostomy or endotracheal tube 18 to assist the patient in breathing. The connector 20 is often referred to as the "15 mm connector" in the art. The connector 32 usually comprises an adhesive patch shown at 34. In order to prevent the ventilator connector 32 from being inadvertently dislodged, a ventilator fastener 26 for positively retaining the connector 32 to the tube 18 is incorporated into the medical tube retention device. The ventilator fastener 26 preferably comprises a soft textile strip 22 or other material suitable for contacting human skin. The ventilator fastener 26 preferably comprises at least one fastening strip 22. A first end 24 of the strip 22 can be affixed to a first end of the neckband 8 and a second end 30 of the strip 22 is constructed to releasably fasten to the second end of the neckband 8. The second end 30 preferably has a hook face (Velcro) surface 28. Preferably, the strip 22 comprises a non-hook, textile and a hook fastening strip 28 on the distal end used to affix to outer layer 4 of the neckband 8. For example, the hook fastening strip 28 can be 1-5 inch, preferably 3 inch in length. Thus, in the preferred embodiment, the majority of the length of the strip 22 comprises a textile material that is non-irritating to skin, to reduce any possible skin irritation that can be detrimental to already medically compromised patients, with only the distal end having an irritating hook fastening strip 28. Compromised patients are more apt to have vulnerable skin conditions and are less able to fight skin infections should they occur. Suitable textiles and foam materials for use on patients are now well known and any well known textile and foam material can be used to form the neckband 8, strip 10 and strip 22.

The strip 22 is preferably has a length sufficient to wrap around and encircle the connector 32 and have the hook 28 affix to the outer layer 4. The strip 22 can be affixed to the connector 32 using the adhesive patch 34 as shown in FIG. 2. FIG. 3 shows the strip 22 being used without an adhesive patch 34.

While the claimed invention has been described in detail and with reference to specific embodiments thereof, it will be apparent to one of ordinary skill in the art that various changes and modifications can be made to the claimed invention without departing from the spirit and scope thereof.

We claim:

1. A device for securing a medical tube comprising a tracheostomy or endotracheal tube and a slotted flange having a first and a second slot, said device constructed to retain the medical tube to a ventilator tube connector, the device comprising:
    a neckband having a first and a second end, the neckband comprising an interior foam material, an inner textile surface suitable for placement against human skin, and an outer textile fastening material;
    a neckband fastening strip having a first end and a second end, the first end of the neckband fastening strip being connected to the first end of the neckband, the neckband and neckband fastening strip having a length sufficient to encircle a human neck, a majority of a length of the neckband fastening strip comprising a non-hook, textile material, the second end of the neckband fastening strip having a hook face surface constructed to releasably fasten to the outer textile fastening material, the second end of the neckband fastening strip being tapered and the neckband fastening strip being sized for insertion into the first and second slots when the flange is pediatric sized; and
    a ventilator fastener comprising a textile strip having a first end and second end, the textile strip comprising an inner surface that is suitable for placement against skin, the first end of the ventilator fastener being connected to the first end of the neckband, the second end of the ventilator fastener constructed to releasably fasten to the outer textile fastening material, and the ventilator fastener having a length sufficient to encircle a connector and have the second end of the ventilator fastener fasten to the outer textile fastening material.

2. A device according to claim 1, wherein a majority of a length of the ventilator fastener being free of a hook surface and the second end of the ventilator fastener comprises a hook surface.

3. A method of securing a medical tube comprising a tracheostomy or endotracheal tube and a slotted flange having a first and a second slot using a device, the method comprising:
    providing the device comprising:
        a neckband having a first and a second end, the neckband comprising an interior foam material, an inner textile surface suitable for placement against human skin, and an outer textile fastening material;
        a neckband fastening strip having a first end and a second end, the first end of the neckband fastening strip being connected to the first end of the neckband, the neckband and neckband fastening strip having a length sufficient to encircle a human neck, the neckband fastening strip comprising a non-hook, textile material, the second end of the neckband fastening strip having a hook face surface constructed to releasably fasten to the outer textile fastening material, the second end of the neckband fastening strip being tapered and the neckband fastening strip being sized for insertion into the first and second slots when the flange is pediatric sized; and
        a ventilator fastener comprising a textile strip having a first end and second end, the textile strip comprising an inner surface that is suitable for placement against skin, the first end of the ventilator fastener being connected to the first end of the neckband, the second end of the ventilator fastener constructed to releasably fasten to the outer textile fastening material, and the ventilator fastener having a length sufficient to encircle a connector and have the second end of the ventilator fastener fasten to the outer textile fastening material;
    cutting the neckband to fit a patient's neck if the neckband is too long for the patient;
    placing the neckband fastening strip through slots in the flange and fastening the second end of the fastening strip to the second end of the neckband so that the portion of the fastening strip in contact with the patient's skin is free of a hook surface; and
    wrapping the ventilator fastener around the connector and fastening the second end of the ventilator fastener to the second end of the neckband so that the portion of the ventilator fastener in contact with the patient's skin is free of a hook surface.

* * * * *